United States Patent
Padma-Nathan et al.

(10) Patent No.: US 11,717,495 B2
(45) Date of Patent: Aug. 8, 2023

(54) USE OF CANNABINOIDS IN TREATING ANTI-DEPRESSANT-INDUCED FEMALE SEXUAL DYSFUNCTION

(71) Applicant: VELLA BIOSCIENCE, INC., Worcester, MA (US)

(72) Inventors: Harin Padma-Nathan, Los Angeles, CA (US); MIchael Frid, Medford, MA (US); Helen Segil, Worcester, MA (US); Nial Chase DeMena, Worceseter, MA (US)

(73) Assignee: Vella Bioscience, Inc., Worcester, MA (US)

( * ) Notice: Subject to any disclaimer, the term of this patent is extended or adjusted under 35 U.S.C. 154(b) by 0 days.

(21) Appl. No.: 17/165,002

(22) Filed: Feb. 2, 2021

(65) Prior Publication Data
US 2021/0283069 A1 Sep. 16, 2021

Related U.S. Application Data

(60) Provisional application No. 62/990,026, filed on Mar. 16, 2020.

(51) Int. Cl.
| | |
|---|---|
| *A61K 31/05* | (2006.01) |
| *A61K 31/5575* | (2006.01) |
| *A61K 36/88* | (2006.01) |
| *A61K 31/4985* | (2006.01) |
| *A61K 31/417* | (2006.01) |
| *A61K 38/12* | (2006.01) |
| *A61K 31/352* | (2006.01) |
| *A61K 9/127* | (2006.01) |
| *A61P 15/10* | (2006.01) |
| *A61K 9/00* | (2006.01) |
| *A61K 31/55* | (2006.01) |
| *A61K 31/137* | (2006.01) |
| *A61K 31/53* | (2006.01) |
| *A61K 31/506* | (2006.01) |
| *A61K 31/519* | (2006.01) |
| *A61K 31/568* | (2006.01) |
| *A61K 31/13* | (2006.01) |
| *A61K 31/475* | (2006.01) |
| *A61K 31/496* | (2006.01) |
| *A61K 31/4458* | (2006.01) |
| *A61K 31/472* | (2006.01) |

(52) U.S. Cl.
CPC ............ *A61K 31/05* (2013.01); *A61K 9/0034* (2013.01); *A61K 9/127* (2013.01); *A61K 31/13* (2013.01); *A61K 31/137* (2013.01); *A61K 31/352* (2013.01); *A61K 31/417* (2013.01); *A61K 31/4458* (2013.01); *A61K 31/472* (2013.01); *A61K 31/475* (2013.01); *A61K 31/496* (2013.01); *A61K 31/4985* (2013.01); *A61K 31/506* (2013.01); *A61K 31/519* (2013.01); *A61K 31/53* (2013.01); *A61K 31/55* (2013.01); *A61K 31/5575* (2013.01); *A61K 31/568* (2013.01); *A61K 36/88* (2013.01); *A61K 38/12* (2013.01); *A61P 15/10* (2018.01)

(58) Field of Classification Search
CPC ...... A61K 9/0034; A61K 9/127; A61K 31/05; A61K 31/13; A61K 31/137; A61K 31/417; A61K 31/4458; A61K 31/472; A61K 31/475; A61K 31/496; A61K 31/4985; A61K 31/506; A61K 31/519; A61K 31/53; A61K 31/55; A61K 31/5575; A61K 31/568; A61K 36/88; A61K 38/12; A61P 15/00; A61P 15/02; A61P 15/12
See application file for complete search history.

(56) References Cited

U.S. PATENT DOCUMENTS

| | | | | |
|---|---|---|---|---|
| 2001/0051656 A1* | 12/2001 | Place | ................. | A61K 2300/00 514/530 |
| 2020/0009107 A1* | 1/2020 | Jenn | ...................... | A61K 31/05 |
| 2020/0016116 A1 | 1/2020 | Epstein | | |

OTHER PUBLICATIONS

Higgins et al., "Antidepressant-associated sexual dysfunction: impact, effects, and treatment", 2010, Drug, Healthcare and Patient Safety, vol. 2, pp. 141-150. (Year: 2010).*
Lorenz, et al. "Antidepressant-induced Female Sexual Dysfunction." Mayo Clinic proceedings vol. 91, 9 (2016).
Study to Evaluate the Efficacy/Safety of Bremelanotide in Premenopausal Women With Hypoactive Sexual Desire Disorder (HSDD), laso found at: clinicaltrials.gov/ct2/show/NCT02333071.
"Female Sexual Dysfunction: New Treatments on the Way" (MGH Center for Women's Mental Health) May 15, 2018 (May 15, 2018) [Retrieved on May 6, 2021] Retrieved for Internet <URL:https://womensmentalhealth.org/posts/female-sexual-dysfunction-new-treatments-on-the-way/>, especially page 2.
Bala, et al. "Post-SSRI Sexual Dysfunction: A Literature Review". Sexual Medicine Reviews. vol. 6 (2018): pp. 29-34 Retrieved on May 6, 2021] Retrieved for Internet <URL:https://www.smr.jsexmed.org/action/showPdf?pii=S2050-0521%2817%29300072-0>, especially p. 29.
Moore and Mattison, Adult Utilization of Psychiatric Drugs and Differences by Sex, Age, and Race., JAMA Int Med. 2017.
Munarriz, et al., "A Review of the Physiology and Pharmacology of Peripheral (Vaginal and Clitoral) Female Genital Arousal in the Animal Model.", The Journal of Urology, vol. 170, S40-545 Aug. 2003.
Hartmann, U., "Depression and Sexual Dysfunction", Mayo Clinic Proc., JMHG, vol. 4, No. 1, pp. 18-25, Mar. 2007.
(Continued)

*Primary Examiner* — Michael B. Pallay
(74) *Attorney, Agent, or Firm* — IP Supra, PLLC; Constantine Linnik

(57) ABSTRACT

The invention relates to compositions and methods containing hemp and/or *Cannabis*-derived cannabidiol (CBD) for topical use in treating female sexual dysfunction induced by antidepressants, including, e.g., selective serotonin reuptake inhibitors (SSRIs), serotonin/norepinephrine reuptake inhibitors (SNRIs), and other anti-depressants.

28 Claims, No Drawings

(56) References Cited

OTHER PUBLICATIONS

Francois, et al., "Antidepressant-Induced Sexual Side Effects: Incidence, Assessment, Clinical Implications, and Management", Psychiatric Annals, vol. 47, No. 3, 2017.
Clayton et al., "Antidepressants and Sexual Dysfunction. Mechanisms and Clinical Complications", Postgraduate Medicine, vol. 126, Issue 2, Mar. 2014, ISSN-0032-5481, e-ISSN-1941-9260.
Lee, et al., "Antidepressant-Induced Sexual Dysfunction among Newer Antidepressants in a Naturalistic Setting", Psychiatry Investigation 2010; 7:55-59.
Lynn, et al., "Effects of Cannabinoids on Female Sexual Function", Sex Med Rev 2019;1-10.
Osis and Bishop, "Pharmacogenetics of SSRIs and Sexual Dysfunction", Pharmaceuticals 2010, 3, 3614-3628; doi:10.3390/ph3123614.
Jakubovic, et al., "Effects of Cannabinoids on Testosterone and Protein Synthesis in Rat Testis Leydig Cells in Vitro", Molecular and Cellular Endocrinology, 15 (1979) 41-50.
Tamblyn et al, "Multinational Comparison of New Antidepressant Use in Older Adults: A Cohot Study", BMJ Open 2019; 9e027663. doi:10.1136/bmjopen-2018-027663.
Stevenson and Bishop, "Genetic determinants of selective serotonin reuptake inhibitor related sexual dysfunction", Pharmacogenomics (2014) 15(14), 1791-1806, ISSN 1462-2416.
Shelton, R.C., "Serotonin Norepinephrine Reuptake Inhibitors: Similarities and Differences", Primary Psych 2009; 16:5 (Suppl 4):25-35.
Stryjer et al., "Trazodone for the Treatment of Sexual Dysfunction Induced by Serotonin Reuptake Inhibitors: A preliminary Open-Label Study", Clinical Neuropharmacology, vol. 32, No. 2, Mar./Apr. 2009.
Jing and Straw-Wilson, "Sexual Dysfunction in Selective Serotonin Reuptake Inhibitors (SSRIs) and Potential Solutions: A Narrative Literature Review", Mental Health Clinician, a publication of the College of Psychiatric and Neurologic Pharmacists, (2016).
Nurnberg, H.G, MD, et al., Sildenafil Treatment of Women With Antidepressant-Associated Sexual Dystunction a Randomized Controlled Trial, American Medical Association (2008) Downloaded from: https://jamanetwork.com/ on May 3, 2021.
Katz, Molly, MD, et al., "Efficacy of Flibanserin in Women with Hypoactive Sexual Desire Disorder: Results from the Begonia Trial", International Society for Sexual Medicine, J Sex Med 2013:10:1807-1815.
Fooladi E., MSC., et al., "Testosterone Improves Antidepressant-Emergent Loss f Libido in Women: Findings from a Randomized, Double-Blind, Placebo-Controlled Trial", International Society for Sexual Medicine, J Sex Med 2014:11:831-839.
English C., et al., "Flibanserin (Addyi) The First FDA-Approved Treatment for Female Sexual Interest/Arousal Disorder in Premenopausal Women", Drug Forecast, vol. 42 No. 4, Apr. 2017.
Rosen, et al., The Female Sexual Function Index (FSFI): A Potential "Gold Standard" Measure for Assessing Therapeutically-Induced Change in Female Sexual Function, Fertility & Sterility, P-145, Tuesday, Oct. 20, 2009, found at: www.fertstert.org/action/showPdf?pii=S0015-0282(09)02741-1/).
International Search Report/Written Opinion for PCT/US2021/022199 dated May 25, 2021.
Response to Written Opinion of the International Searching Authority for PCT/US2021/22199 dated Jul. 26, 2021.
Hermann et al., (1990) Fluoxetine-induced sexual dysfunction, Journal of Clinical Psychiatry 51, 25-27.
Shen W. W., Urosevich, Z., and Clayton, D. O. (1999) Sildenafil in the treatment of female sexual dysfunction induced by selective serotonin reuptake inhibitors, Journal of Reproductive Medicine 44, 535-542. Abstract only: https://pubmed.ncbi.nlm.nih.gov/10394548/.
Kaplan, S. A., Reis, R. B., Kohn, I. J., Ikeguchi, E. F., Laor, E., Te, A. E., and Martins, A. C. (1999) Safety and efficacy of sildenafil in postmenopausal women with sexual dysfunction, Urology 53, 481-486. Abstract only.
Michelson, David M.D., Bancroft John, M.D., Targum, Steven, M.D., Kim Yongman, Ph.D., and Tepner Rosalinda, R.Ph., "Female Sexual Dysfunction Associated with Antidepressant Administration: A Randomized, Placebo-Controlled Study of Pharmacologic Intervention". American Journal Psychiatry 157:2, Feb. 2000.
Woodrum, Sharton T. and Brown, Candace S., "Management of SSRI-Induced Sexual Dysfunction", The Annals of Pharmachotherapy, vol. 32, Nov. 1998.
Jespersen, Sean, et al., "A pilot randomized, double-blind, placebo-controlled study of granisetron in the treatment of sexual dysfunction in women associated with antidepressant use", International Clinical Psychopharmacology, vol. 19, No. 3, 2004.
Metson, Cindy M., "A Randomized, Placebo-Controlled, Crossover Study of Ephedrine for SSRI-Induced Female Sexual Dysfunction", Journal of Sex & Marital Therapy, 30:57-68, 2004; DOI: 10.1080/00926230490247093.
Nurnberg, George H., M.D., et al., "Sildenafil for women patients with antidepressant-induced sexual dysfunction", Psychiatric Services vol. 50, No. 8, Aug. 1999.
Ashton, Adam Keller, et al., "Serotonin Reuptake Inhibitor-Induced Sexual dysfunction and its treatment: a large-scale retrospective study of 596 psychiatric outpatients", Journal of Sex & Marital Therapy, vol. 23, No. 3, Fall 1997.
Baldwin, David, et al., "Slective serotonin re-uptake inhibitor treatment-emergent sexual dysfunction: randomized double-blind placebo-controlled parallegl-group fixed-dose study of a potential adjuvant compound, VML-670", Journal of Psychopharmacoloy (22(1) (2008) 55-63.
Luft, Marissa J. et al., "Pharmacologic interventions for antidepressant-induced sexual dysfunction: a systematic review and network meta-analysis of trials using the Arizona sexual experience scale", Cambridge University Press, CNS Spectrums, https://doi.org/10.1017/S1092852921000377.
Serretti, Alessandro, et al., "Treatment-emergent sexual dysfunction related to antidepressants", Journal of Clinical Psychopharmacology, vol. 29, No. 3, Jun. 2009.
Brown, Dana A., et al, "Assessing the clinical efficacy of sildenafil for the treatment of female sexual dysfunction", The Annals of Pharmacotherapy, vol. 43 Jul./Aug. 2009.
Clayton, AH, et al. (2016) Characterizing sexual function in patients with generalized anxiety disorder: a pooled analysis of three vilazodone studies, Neuropsychiatric Disease and Treatment 12, 1467-1476.
Tuiten, A, et al. (2018) Efficacy and Safety of On-Demand Use of 2 Treatments Designed for Different Etiologies of Female Sexual Interest/Arousal Disorder: 3 Randomized Clinical Trials, Journal of Sexual Medicine 15, 201-216.
Clayton, AH, et al. (2014) Sexual dysfunction associated with major depressive disorder and antidepressant treatment, Expert Opinion on Drug Safety 13, 1361-1374.
Clayton, AH, et al. (2016) Sexual dysfunction due to psychotropic medications, Psychiatric Clinics of North America 39 (3), 427-463.
Lynn, B, et al. (2020) Effects of Cannabinoids on Female Sexual Function, Sexual Medicine Reviews 8, 18-27.
Nurnberg, HG, et al. (2008) Sildenafil treatment of women with antidepressant-associated sexual dysfunction: a randomized controlled trial, Journal of American Medical Association 300, 395-404.
Healy, D. (2018) Citizen petition: Sexual side effects of SSRIs and SSRIs, International Journal of Risk & Safety in Medicine 29, 135-147.

\* cited by examiner

USE OF CANNABINOIDS IN TREATING ANTI-DEPRESSANT-INDUCED FEMALE SEXUAL DYSFUNCTION

FIELD OF THE INVENTION

The invention relates to compositions and methods containing hemp and/or *Cannabis*-derived cannabidiol (CBD) for topical use in treating female sexual dysfunction secondary to treatment with selective serotonin reuptake inhibitors (SSRIs), serotonin/norepinephrine reuptake inhibitors (SNRIs), and other anti-depressants.

BACKGROUND

The 12-month prevalence of major depressive disorder (MDD) in the United States has been estimated at 6.7%, with 30.4% of cases classified as serious. Relative to men, the odds ratio for women developing MDD in a 12-month period or during their lifetime is 1.4 and 1.7, respectively (Clayton, A. H., et al. (2014). "Antidepressants and sexual dysfunction: mechanisms and clinical implications." Postgraduate Medicine 126(2): 91-99). Unsurprisingly, antidepressant use in the United States is also widespread. In a recent study, 15.9% (14.8-17.0) of women in the US reported filling at least one prescription for an antidepressant medication in 2013 and most use of antidepressants was long-term (Moore, T. J. and D. R. Mattison (2017). "Adult Utilization of Psychiatric Drugs and Differences by Sex, Age, and Race." JAMA Internal Medicine 177(2): 274-275).

Selective serotonin reuptake inhibitors (SSRIs) and serotonin/norepinephrine reuptake inhibitors (SNRIs) are effective at relieving symptoms of depression and generally are better tolerated than other classes of antidepressants. However, SSRIs and SNRIs use is associated with sexual dysfunction (SD). Antidepressant-induced SD has been reported in up to 70% of patients treated with SSRIs or SNRIs, and these side effects, generally, are persistent and do not abate with continued treatment, and in some cases persist after discontinuation of treatment. The most commonly reported adverse sexual effects in women taking antidepressants are problems with sexual desire (72%) and sexual arousal (83%). Approximately 42% of women taking selective serotonin reuptake inhibitors report problems having an orgasm (Lorenz, T., et al. (2016). "Antidepressant-Induced Female Sexual Dysfunction." Mayo Clinic Proceedings 91(9): 1280-1286). These data must be viewed in comparison with untreated depression, which also is associated with increased levels of SD, affecting one or more of the aspects of sexual response—desire, arousal, or orgasm. It suggested that in women hypoactive sexual desire is the dominant sexual dysfunction associated with untreated depression (Hartmann, U. (2007). "Depression and sexual dysfunction." Journal of Men's Health and Gender 4(1): 18-25) whereas dysfunction in other aspects of sexual response is more prevalent in antidepressant-induced SD (Jing, E. and K. Straw-Wilson (2016). "Sexual dysfunction in selective serotonin reuptake inhibitors (SSRIs) and potential solutions: A narrative literature review." Mental Health Clinician 6(4): 191-196; Francois, D., et al. (2017). "Antidepressant-Induced Sexual Side Effects: Incidence, Assessment, Clinical Implications, and Management." Psychiatric Annals 47(3): 154-160).

The antidepressant-induced SD may exacerbate depression symptoms and is frequently cited as a reason for nonadherence or discontinuation of treatment for depression; some 15% of women fall into this category according to one estimate (Jing, E. and K. Straw-Wilson (2016). "Sexual dysfunction in selective serotonin reuptake inhibitors (SSRIs) and potential solutions: A narrative literature review." Mental Health Clinician 6(4): 191-196). Moreover, onset of sexual side effects may occur within 1-3 weeks after initiation of therapy and this may precede the onset of clinical antidepressant activity.

Selective serotonin reuptake inhibitors (SSRIs) are recommended as part of the first line treatment of Major Depressive Disorder (MDD). SSRIs and serotonin/norepinephrine reuptake inhibitors (SNRIs) are most frequently used antidepressants in the United States and Canada, and are highly prevalent elsewhere. In 2013, five of the 10 most prescribed psychiatric drugs belonged to the SSRI or SNRI class (Moore, T. J. and D. R. Mattison (2017), supra) and all of these drug substances (sertraline, citalopram, fluoxetine, escitalopram, and duloxetine) have a varying but significant likelihood of causing SD. A non-exhaustive list of SSRI and SNRI drugs known to cause sexual dysfunction is shown in Table 1.

TABLE 1

Examples of commonly prescribed SSRIs and SNRIs known to cause sexual dysfunction side effects (brand name or one of multiple brand names)

| | |
|---|---|
| Sertraline (Zoloft ®) | SSRI |
| Fluoxetine (Prozac ®) | SSRI |
| Citalopram (Celexa ®) | SSRI |
| Escitalopram (Lexapro ®) | SSRI |
| Duloxetine (Cymbalta ®) | SNRI |
| Venlafaxine (Effexor ®) | SNRI |
| Desvenlafaxine (Pristiq ®) | SNRI |
| Paroxetine (Paxil ®) | SSRI |
| Fluvoxamine (Luvox ®) | SSRI |

Tricyclic and the related tetracyclic antidepressants, while largely supplanted as first line medications for the treatment of clinical depression, are still in use, and are more common in some countries other than in the US (Tamblyn, R., et al. (2019) Multinational comparison of new antidepressant use in older adults: a cohort study, BMJ open 9, e027663). This class of antidepressants also is well known to cause sexual dysfunction. A non-exhaustive list of tricyclic and tetracyclic antidepressants known to cause sexual dysfunction is shown in Table 2. It should be noted that even the drugs classified as "less likely" or "unlikely" to cause SD, such as mirtazapine, still do produce SD side effects relative to placebo but in smaller percentage of patients by comparison with other antidepressants of the same class (Lee, K.-U., et al. (2010) Antidepressant-Induced Sexual Dysfunction among Newer Antidepressants in a Naturalistic Setting, Psychiatry Investigation 7, 55-59).

TABLE 2

Marketed tricyclic and tetracyclic antidepressants known to cause sexual dysfunction side effects (brand name or one of multiple brand names)

| | |
|---|---|
| Clomipramine (Anafranil ®) | tricyclic |
| Trimipramine (Surmontil ®) | tricyclic |
| Amitriptyline (Elavil ®) | tricyclic |
| Desipramine (Norpramin ®) | tricyclic |
| Imipramine (Tofranil ®) | tricyclic |
| Doxepin (Sinequan ®) | tricyclic |
| Nortriptyline (Aventyl ®) | tricyclic |
| Protriptyline (Vivactil ®) | tricyclic |
| Maprotiline (Ludiomil ®) | tetracyclic |
| Mirtazapine (Remeron ®) | tetracyclic |

Thus, a substantial number of patients might benefit from efforts to reduce or prevent the development of SD during use of antidepressant therapy.

As noted, antidepressant-induced SD largely affects the "mechanical" aspects of sexual function and in women results in decreased arousal/lubrication and delayed orgasm, difficulties reaching orgasm, or in anorgasmia. The mechanism by which SSRIs and SNRIs cause sexual dysfunction is unknown and is subject of debate. Neurotransmitters, such as serotonin (5-hydroxytryptophan), dopamine, and norepinephrine, are involved in the physiology of sexual functioning as well as in governing mood and antidepressants may increase or decrease the levels and function of these neurotransmitters. Dopamine is reportedly related to motivated behaviors, including sexual behaviors, whereas norepinephrine stimulates sexual arousal and vasocongestion. However, activation of serotonin systems results in suspension of vasocongestion, thus diminishing arousal mechanisms in genital organs; the action of serotonin may also decrease nitric oxide function and genital sensation. Other neurotransmitters and hormones may be involved, such as glutamate, testosterone, and estrogen. The antidepressant-induced SD is dose dependent and may be influenced by an individual's levels of enzymes responsible for metabolizing a SSRI or a SNRI drug substance. It is postulated that the most common antidepressants, SSRIs and SNRIs, have similar CNS mechanisms of causing sexual dysfunctions, by elevating serotonin, however, the interplay of several signaling systems involved in arousal and orgasm is complex, and there is no clear biomarker of susceptibility to antidepressant-induced sexual dysfunction (Osis, L. and J. R. Bishop (2010). "Pharmacogenetics of SSRIs and Sexual Dysfunction." Pharmaceuticals 3(12): 3614-3628; Stevenson, J. M. and Bishop J. R. (2014). "Genetic determinants of selective serotonin reuptake inhibitor related sexual dysfunction." Pharmacogenomics 15(14): 1791-1806). Notably, the distinction between SSRIs and SNRIs is not always clear-cut, as some antidepressants classified as SNRIs, such as duloxetine, venlafaxine, and desvenlafaxine are selective for inhibition of serotonin reuptake over norepinephrine reuptake and act as SSRIs at low doses (Shelton, R. C. (2009). Serotonin norepinephrine reuptake inhibitors: similarities and differences. Primary Psychiatry 16(4): 25). The mechanisms by which tricyclic and tetracyclic antidepressants affect sexual function also are unclear although the majority of tricyclic and tetracyclic antidepressants are believed to exert antidepressant and anxiolytic affects similarly to SNRIs, by inhibition of serotonin and norepinephrine reuptake.

The current management of SSRI and SNRI associated sexual dysfunctions reflects the poor response and lack of effective pharmacologic therapies to address them. It includes: (1) rule out other possible causes, (2) wait and see, (3) change the time the antidepressant medication is taken, (4) drug holidays, (5) decrease the dose of the medication, (6) switch to or add mirtazapine, (7) switch to or add bupropion, (8) add phosphodiesterase inhibitors (sildenafil or tadalafil), (9) try topical testosterone, (10) try amantadine, (11) try yohimbine, (12) switch to or add trazodone, (13) try stimulants such as methylphenidate, (14) behavioral therapy, (15) try dietary supplements such as saffron, and (16) acupuncture. In short, a female patient who suffers from a SSRI or SNRI related SD has few effective options and many discontinue treatment as a result of the SD, which can have disastrous consequences.

$\Delta^9$-(delta 9)-tetrahydrocannabinol (THC) was the first cannabinoid identified from the *Cannabis sativa* plant and characterized in the 1960's by Mechoulam and associates. It is a potent sedative-hypnotic. Subsequently, over a hundred cannabinoids, including cannabidiol (CBD), a non-psychoactive cannabinoid, have been identified. CBD has been attributed to have many potential pharmacological benefits in pain, inflammation and, most recently, in infantile seizure disorders. To date, there have been no scientific studies to explore the potential of cannabinoids and specifically of cannabidiol (CBD) in the management of antidepressant-induced sexual dysfunction. The endocannabinoid system (ECS) is a major neuromodulatory regulatory system found in the central nervous system and in select peripheral nerves and organs. It is made up of cannabinoid (CB1 and CB2) receptors, their endogenous ligands (endocannabinoids: anandamide (AEA) and 2-arachidonoylglycerol), proteins involved in the synthesis and breakdown of endocannabinoids, and the intracellular signaling pathways affected by cannabinoids. CB1 and CB2 receptors are G-protein-coupled receptors that serve as the primary sites of action for cannabinoids. The cannabinoid receptors differ in their distribution. CB1 receptors are found throughout the central nervous system and some peripheral tissues. Cannabinoid receptors in the CNS are found in the hypothalamus, hippocampus, amygdala, cerebral cortex, parts of the basal ganglia, and cerebellum. CB1 and CB2 receptors are pre-synaptic receptors that results in inhibition of neurotransmitter release when activated. CB1 receptors are located in the axon terminals of GABAergic, dopaminergic, adrenergic, glutamatergic, cholinergic and some serotonergic neurons, particularly in the primitive portions of the limbic system that control, among other things, sexual behavior. Peripherally, CB2 cannabinoid receptors are found in organs responsible for producing sex hormones. They have also been found in the ovaries, uterus, bladder, penile corpora and the testes. To date, there are no published reports on identification and distribution of CB receptors in vagina and clitoris.

The role of the hypothalamic pituitary axis on female sex hormones and thus female sexual function has been long established. The neurohormonal aspects of male and female sexual desire or interest are driven by androgens. The endocannabinoid system appears to be inhibitory to sexual responses in animals. Levels of the endocannabinoids anandamide (AEA) and 2-arachidonoylglycerol (2-AG) are lowered in response to sexual stimulation and spike after climax. THC appears to blunt the activation of hormones that modulate female sexual responses in animal and human studies. Exogenous THC, in the presence of an intact hormonal axis, produces female rat lordosis (a sexual receptivity posture) at low doses and human studies generally bear out positive effect of low to moderate doses of THC on female sexual function, more specifically on sexual desire and satisfaction. This is believed to be an entirely central nervous system effect and not a peripheral response. While CB1 and CB2 receptors for endocannabinoids exist peripherally, the actions of THC on sexual function are believed to be central in action on the dopaminergic and serotonergic pathways of the limbic system (hypothalamic ventral tegmental area and nucleus accumbens). Pharmacologic doses of THC appear to augment these serotonergic and dopaminergic pathways (Lynn, B., et al. (2020) Effects of Cannabinoids on Female Sexual Function, Sexual Medicine Reviews 8, 18-27).

In contrast to desire, sexual arousal is a peripheral genital process. Female and male sexual arousal, as evidenced by clitoral engorgement and vaginal lubrication or penile erection, respectively, are regulated by the tone of the smooth muscle of the clitoris and vagina, and by the tone of the smooth muscle of the corpora cavernosa and corpus spongiosum. Despite identification of CB2 receptors in ovaries and endometrial tissue, there have been no published studies to identify the presence of vaginal or clitoral CB receptors in animal or human tissue and thus no prior scientific evidence to support a role for cannabinoids, such as cannabidiol, to effect arousal through a peripheral pharmacologic action on this smooth muscle. To date, there have been no published reports on examinations of a direct pharmacologic effect of any individual cannabinoid on vaginal or clitoral smooth muscle function, such as the standard studies in rat and human vaginal tissue to demonstrate a pharmacologic impact on smooth muscle and its related endothelium, which are usually performed in isolated tissue organ baths, examining the dose or concentration related relaxations responses (lowered isometric tension) in pre-contracted smooth muscle tissue (Munarriz, R., et al. (2003) A review of the physiology and pharmacology of peripheral (vaginal and clitoral) female genital arousal in the animal model, Journal of Urology 170, S40-44). Furthermore, systemic administration of cannabinoids is deemed to have high potential for adverse drug-drug interactions with some medications, including tricyclic and tetracyclic antidepressants.

Considering the known pharmacology of CBD, it is counterintuitive that administration of CBD should have any effect in countering the antidepressant-induced sexual dysfunction. For example, there is clinical evidence that the addition of trazodone to a SSRI antidepressant may mitigate the SSRI-induced SD (Stryjer, R., et al. (2009) Trazodone for the Treatment of Sexual Dysfunction Induced by Serotonin Reuptake Inhibitors: A Preliminary Open-Label Study, Clinical neuropharmacology 32, 82-84). It is believed that trazodone exerts its effects via antagonism of the $5\text{-HT}_{2A}$ receptor. Trazodone also is an antagonist of the α1-adrenergic receptor and the $5\text{-HT}_{1A}$ receptor. Similarly, yohimbine is prescribed to treat antidepressant-induced SD and is an antagonist of $5\text{HT}_{2A}$ receptor. By contrast, CBD is a weak agonist of the $5\text{-HT}_{2A}$ receptor and, therefore, would not be expected to produce similar pharmacological effects irrespective of the route of administration, whether oral or topical. Furthermore, in rodent studies CBD acted peripherally to decrease testosterone levels by inhibiting its biosynthesis and accelerating its metabolism (Jakubovic, A., et al. (1979). "Effects of cannabinoids on testosterone and protein synthesis in rat testis leydig cells in vitro." Molecular and Cellular Endocrinology 15(1): 41-50). With the exception of topical testosterone, all of the pharmacological approaches to treatment of antidepressant-induced SD involve oral administration of drugs, i.e., systemic therapy. However, systemic administration of cannabinoids is deemed to have high potential for adverse drug-drug interactions with some medications, including tricyclic and tetracyclic antidepressants. There is no a priori reason to believe that local (peripheral) administration of CBD would be effective in treating or modulating the antidepressant-induced sexual dysfunction.

Accordingly, there remains a need to provide new methods of treating antidepressant-induced female SD.

SUMMARY OF THE INVENTION

The present invention is based, at least in part, on the observation that cannabidiol (CBD)-containing composition, when administered topically to the mucosal surface of the female genital area, is able to ameliorate female sexual dysfunction induced by antidepressants. The invention is further based, at least in part, on the discovery that, contrary to the topically administered CBD, systemic administration of CBD, or topical administration of THC in a formulation similar to that of CBD, are not effective in amelioration of that condition.

The present disclosure provides peripherally acting CBD-containing compositions and methods of using thereof for treating female sexual dysfunction secondary to treatment with antidepressants (antidepressant-induced sexual dysfunction). In some embodiments, the female sexual dysfunction is induced by SSRIs, SNRIs, tricyclic, or tetracyclic antidepressants. In some embodiments, the female sexual dysfunction is related to arousal and/or lubrication, including but not limited to difficulty in achieving and maintaining engorgement, and difficulty in achieving and maintaining lubrication. In some embodiments, the female sexual dysfunction is related to orgasm, including but not limited to, difficulty achieving orgasm, low orgasm intensity, or anorgasmia. In some embodiments, the female sexual dysfunction is related to lack of interest or desire. In general, the compositions of the invention are applied as a lotion or a similar formulation in the amount and for a period of time prior to a sexual activity such that sexual function of the subject is enhanced and/or the SD is ameliorated during the sexual activity, for example, as exhibited by either objective parameters (vaginal and clitoral smooth muscle relaxation and/or increased vaginal and clitoral blood flow) or improvements in self-reported outcomes such as: "increased lubrication/wetness during sexual activity"; "reaching orgasm" if anorgasmic after starting antidepressant therapy, "reaching orgasm more often"; "greater ease of achieving orgasm"; "being more satisfied"; "higher level of sexual desire"; and "reduction in pain during sexual activity". In other embodiments, the compositions of the invention are applied as lotion in the amount and for a period of time prior to a sexual activity such that sexual function of the subject is enhanced and/or the disorder is ameliorated during the sexual activity, such that some proportion of sexual function of the subject lost due to antidepressant-induced sexual dysfunction is recovered to levels experienced prior to starting antidepressant therapy, or is enhanced, if the subject was not sexually active prior to starting antidepressant therapy, said improvements determined using questionnaires derived from the Female Sexual Function Index questionnaire (FSFI) or the Arizona Sexual Experiences Scale (ASEX) questionnaire, or equivalent.

In some embodiments, the subjects are premenopausal women, while in other embodiments the subjects are postmenopausal women.

DETAILED DESCRIPTION OF THE INVENTION

The present disclosure provides peripherally acting cannabidiol (CBD)-containing compositions and methods of using thereof for treating female sexual dysfunction secondary to treatment with antidepressants (antidepressant-induced sexual dysfunction), whether or not the antidepressants are used in the treatment of MDD or other depressive spectrum disorders (persistent depressive disorder or dysthymia, melancholic depression, etc.), anxiety disorders such as generalized anxiety disorder (GAD) and social anxiety disorder (SAD), attention-deficit hyperactivity disorder (ADHD), obsessive-compulsive disorder (OCD), bulimia nervosa (bulimia), panic disorder, premenstrual dysphoric disorder, menopause-associated vasomotor symptoms, fibromyalgia, neuropathic pain, post-traumatic stress disorder (PTSD), diabetic peripheral neuropathy (DPN), chemotherapy-induced neuropathy, or for the treatment of another indication. In some embodiments, the female sexual dysfunction is related to arousal and/or lubrication, including but not limited to difficulty in achieving and maintaining engorgement, and difficulty in achieving and maintaining lubrication. In some embodiments, the female sexual dysfunction is related to orgasm, including but not limited to difficulty achieving orgasm, low orgasm intensity, or anorgasmia. In some embodiments, the female sexual dysfunction is related to sexual desire or interest. In some embodiments, the subjects are premenopausal women, while in other embodiments the subjects are post-menopausal women.

The female sexual dysfunction can be secondary to treatment with selective serotonin reuptake inhibitors (SSRIs), serotonin norepinephrine reuptake inhibitors (SNRIs), tricyclic antidepressants, and tetracyclic antidepressants. Accordingly, in some embodiments, the female sexual dysfunction is secondary to treatment with SSRIs or SNRIs. In some embodiments, the female sexual dysfunction is secondary to treatment with tricyclic or tetracyclic antidepressants. In some particular embodiments, the female sexual dysfunction is secondary to treatment with sertraline, citalopram, fluoxetine, escitalopram, paroxetine, fluvoxamine, duloxetine, venlafaxine, and desvenlafaxine. In other particular embodiments, the female sexual dysfunction is secondary to treatment with sertraline, citalopram, fluoxetine, escitalopram, paroxetine, and fluvoxamine. In other particular embodiments, the female sexual dysfunction is secondary to treatment with sertraline, citalopram, and fluoxetine. In other particular embodiments, the female sexual dysfunction is secondary to treatment with duloxetine, venlafaxine, desvenlafaxine, milnacipran, and levomilnacipran. In other particular embodiments, the female sexual dysfunction is secondary to treatment with clomipramine, trimipramine, amitriptyline, desipramine, imipramine, lofepramine, doxepin, nortriptyline, amoxapine, and protriptyline. In still other embodiments, the female sexual dysfunction is secondary to treatment with maprotiline and mirtazapine. In general, sexual dysfunction induced by any anti-depressant of the SSRI, SNRI, tricyclic, or tetracyclic classes is susceptible to the treatment/amelioration with the methods of the present invention.

In general, according to the methods of the invention, a composition is applied to the female genitalia shortly prior to sexual activity, thereby resulting in the SD of the subject disorder being ameliorated during the sexual activity, as exhibited, for example, by either objective parameters (e.g., vaginal and clitoral smooth muscle relaxation and/or increased vaginal and clitoral blood flow) or subjective parameters, e.g., improvements in self-reported outcomes such as: "increased lubrication/wetness during sexual activity"; "reaching orgasm more often"; "greater ease of achieving orgasm"; "being more satisfied"; "higher level of sexual desire"; and "reduction in pain during sexual activity".

In preferred embodiments, a composition is applied to the female genitalia shortly prior to sexual activity such that some proportion (e.g., 10%, 20%, 25%, 30%, 35%, 40%, 45%, 50%, 55%, 60%, 65%, 70%, 75%, 80%, 85%, 90%, 95%, or 100%) of sexual dysfunction induced by an antidepressants is recovered to levels experienced prior to starting antidepressant therapy, or is enhanced if the subject was not sexually active prior to starting antidepressant therapy.

Said improvements are determined using questionnaires derived from the Female Sexual Function Index questionnaire (FSFI) or the Arizona Sexual Experiences Scale (ASEX) questionnaire, or equivalent. In some embodiments, the improvement in sexual interest/arousal domain is by 1-2 points, and by 1-2 points in the orgasm domain of the FSFI.

In some embodiments, the amelioration of sexual dysfunction is exhibited by one or both of the following parameters:
    i. vaginal and clitoral smooth muscle relaxation; and
    ii. increased vaginal and clitoral blood flow.
In other embodiments, the amelioration of sexual dysfunction is exhibited by one or more of the following subjectively self-reported outcomes including:
    iii. "increased lubrication/wetness during sexual activity";
    iv. "reaching orgasm more often";
    v. "greater ease or achieving orgasm";
    vi. "being more satisfied";
    vii. "higher level of sexual desire"; and
    viii. "reduction in pain during sexual activity".

In yet further embodiments, a phosphodiesterase type 5 inhibitor such as, for example, sildenafil, tadalafil, vardenafil, avanafil, or udenafil, can be added to the CBD-containing composition.

In yet other embodiments, the subject is concurrently undergoing a treatment with a PDE-5 inhibitor (e.g., sildenafil, tadalafil, vardenafil, avanafil, and udenafil). Such a PDE-5 inhibitor may be administrated orally or topically as a separate topical dosage form before, concurrently, or after the application of the CBD-containing composition, or such a PDE-5 inhibitor and CBD may be formulated in the same dosage form.

In another embodiment, another direct smooth muscle relaxant such as, for example, prostaglandin E1, papaverine, minoxidil, can be added to the CBD-containing composition.

In another embodiment, an alpha-blocker (e.g., phentolamine) can be added to the CBD-containing composition.

In another embodiment, flibanserin can be added to the CBD-containing composition to augment sexual desire.

In another embodiment, bremelanotide can be added to the CBD-containing composition to augment sexual desire.

In further embodiments, the subject has been previously treated with, but did not satisfactorily respond to one or more of the following treatments: (1) change of the time the antidepressant medication is taken, (2) drug holidays, (3) decrease the dose of the medication, (4) switching to or addition of mirtazapine, (5) switching to or addition of bupropion, (6) addition of phosphodiesterase inhibitors (e.g., sildenafil, tadalafil, vardenafil, avanafil, and udenafil), (9) topical testosterone, (7) amantadine, (8) yohimbine, (9) switching to or addition of trazodone, (10) stimulants such as methylphenidate, (11) behavioral therapy, (12) dietary supplements, e.g., saffron, and (13) acupuncture. In yet further embodiments, the administrations of CBD-containing compositions according to the methods of the invention is supplemented with one or more of the aforementioned therapies (1 through 13).

In certain embodiments, the subject was previously treated with an anti-depressant that induced sexual dysfunction and has persistent sexual dysfunction despite discontinuation of the anti-depressant therapy.

As used herein, the term "composition" is used interchangeably with the term "formulation." In general, a "formulation" of the invention comprises CBD and may contain one or more of surfactants, cryoprotectants, bulking agents, stabilizers, emulsifiers, anti-oxidants, water-miscible solvents, oils, lipids, phospholipids, waxes, water-immiscible solvents, anti-microbial agents whether water-soluble or not, or thickeners, and may be formulated as an ointment, a cream, a suspension, a lotion, a paste, a gel, a balm, a tincture, an emulsion, or a serum suitable for application to the female genitalia, the basic preparation techniques of which are known to those skilled in the art. The creams, suspensions, lotions, gels, pastes, etc. may comprise CBD encapsulated into liposomes, which may be large in the micron range or larger, small of below 100 nm, or medium size, may be unilamellar or multilamellar or a mixture of unilamellar and multilamellar, may be formed with lipids of neutral overall charge (zwitterionic) such as HSPC, with lipids of negative net charge such as HSPG, or with lipids of positive net charge, may be stabilized with, for example, cholesterol, or edge-activated by incorporation of surfactants, such as for example Tween 80 or Tween 20, or may be ethosomes, glycerosomes, and PG-liposomes, the basic preparation techniques of which are known to those skilled in the art. Furthermore, the creams, suspensions, lotions, gels, pastes, etc. may comprise CBD encapsulated into an emulsion, for example a nanoemulsion of the oil-in-water type or a double water-in-oil-in-water emulsion, formed by application of energy through high shear stirring, high pressure homogenization, sonication, or other techniques known in the art, or a spontaneously formed microemulsion.

In general, the methods of the invention employ topical compositions that comprise CBD, such that a composition is applied topically to a female subject's genital (arousal) area(s), to surface with absorptive mucosa, such as, for example, the introitus, the labia minora, the clitoris and the vaginal vault. In some embodiments, the compositions are provided in the form of a CBD lotion, which is applied to the female genitalia shortly prior to sexual activity. In preferred embodiments, the compositions are provided in the form of a lotion, containing CBD-loaded liposomes (multilamellar, unilamellar or a mixture thereof), which is applied to the female genitalia shortly prior to sexual activity. In preferred embodiments, the CBD-containing composition is compatible with latex and polyisoprene condoms. In preferred embodiments, CBD-containing composition (referred to as Vella™) also comprises liposomes that comprise HSPC, ascorbic acid, sodium ascorbate, propylene glycol, polyacrylate crosspolymer-6, and water or aqueous buffer, and wherein the liposomes are provided in a homogeneous suspension. While it can be referred to as Vella™ "lotion", such composition can be provided also as lubricant, cream, gel, or another similar formulation as described herein.

As used herein, the term "phospholipid" or "phospholipids" refers to amphiphilic compounds comprising at least one saturated or unsaturated hydrophobic fatty acid moiety and a hydrophilic moiety comprising a phosphate group. These include, for example, dicetyl phosphate, soya phosphatidylcholine (SPC), egg phosphatidylcholine (EPC), hydrogenated soya phosphatidylcholine (HSPC), soya lecithin, hydrogenated soya lecithin, sphingomyelin, dioleoyl phosphatidylcholine (DOPC), dilinoleoyl phosphatidylcholine (DLPC), dioleoyl phosphatidylethanolamine (DOPE), dimyristoyl phosphatidylethanolamine (DMPE), dipalmitoyl phosphatidylethanolamine (DPPE), dimyristoyl phosphatidylcholine (DMPC), dipalmitoyl phosphatidylcholine (DPPC), distearoyl phosphatidylcholine (DSPC), dilauroyl phosphatidylcholine (DLPC), 1-myristoyl-2-palmitoyl phosphatidylcholine, 1-palmitoyl-2-myristoyl phosphatidylcholine, 1-palmitoyl phosphatidylcholine, 1-stearoyl-2-palmitoyl phosphatidylcholine, dipalmitoyl sphingomyelin, distearoyl sphingomyelin, soya phosphatidylinositol (SPI), hydrogenated phosphatidylinositol (HPI), dimyristoyl phosphatidylglycerol (DMPG), dipalmitoyl phosphatidylglycerol (DPPG), distearoyl phosphatidylglycerol (DSPG), dimyristoyl phosphatidic acid (DMPA), dipalmitoyl phosphatidic acid (DPPA), dimyristoyl phosphatidylserine (DMPS), dipalmitoyl phosphatidylserine (DPPS), hydrogenated soya phosphatidylglycerol (HSPG), dioleoyl phosphatidylglycerol (DOPG), distearoyl phosphatidic acid (DSPA), and mixtures thereof, and salts thereof, preferably sodium or ammonium salts. Phospholipids may be present, on weight-to-weight (w/w) basis relative to total weight of a composition, at a level of 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, or 25%. In preferred embodiments, the phospholipid is one of or is a combination of two or more of SPC, EPC, HSPC, or DSPC, more preferably HSPC. In certain embodiments, the liposome constituent lipids do not include cholesterol or its derivatives. In some embodiments, the lipids consist of, or consist essentially of, of the phospholipids recited above, or a subset thereof.

As used herein, the term "cryoprotectant" or "cryoprotectants" or "bulking agent" or "bulking agents" refers to compounds such as, for example, mannitol, sorbitol, lactose, trehalose, sucrose, dextran of different molecular weights such as dextran 40, inulin, glycine, L-arginine, α-cyclodextrin, β-cyclodextrin, γ-cyclodextrin, hydroxypropyl-β-cyclodextrin, hydroxypropyl-γ-cyclodextrin, randomly methylated-β-cyclodextrin, sulfobutyl ether β-cyclodextrin (SBE β-CD), hydroxypropyl methylcellulose (HPMC, hypromellose), methylcellulose, polyvinylpyrrolidone (PVP) K15, K16-18, K30, or K90, citric acid, sodium citrate, poloxamer 188 (Pluronic® F-68), poloxamer 407 (Pluronic® F-127), polyvinyl alcohol of differing degree of de-acetylation and of different viscosities, such as the 4-88 and 5-88 grades, or polyvinyl caprolactam-polyvinyl acetate-polyethylene glycol graft copolymer (Soluplus®).

As used herein, the term "stabilizer" or "stabilizers" refers to, for example, ascorbic acid, ascorbate salts such as sodium or potassium ascorbate, citric acid, citrate salts such as, for example, sodium or potassium citrate, ethylenediaminetetraacetic acid (EDTA), EDTA salts such disodium EDTA, dipotassium EDTA, trisodium EDTA, tetrasodium EDTA, or calcium disodium EDTA, hydroxyethyl ethylenediamine triacetic acid (HEDTA), trisodium HEDTA, diethylenetriaminepentaacetic acid (DTPA), ethylenediamine-N, N'-disuccinic acid (EDDS), trisodium EDDS, DTPA pentasodium salt (pentasodium diethylenetriaminepentaacetate), methylglycinediacetic acid, trisodium dicarboxymethyl alaninate, d-glucono-1,5-lactone, gluconic acid and its salts such as sodium or potassium gluconate, or calcium gluconate, iminodisuccinic acid tetrasodium salt (tetrasodium iminodisuccinate), α-tocopherol, α-tocopherol acetate, ascorbyl palmitate, ascorbyl stearate, butylated hydroxytoluene (BHT), or butylated hydroxyanisole (BHA).

As used herein, the term "water-miscible solvent", "water-miscible solvents", "water-soluble solvent", or "water-soluble solvents" refers to compounds such as, for example, ethyl alcohol (ethanol), t-butyl alcohol (t-butanol, tert-butanol, or TBA), polyethylene glycols (PEGs or macrogols) of different molecular weights such as PEG 300, PEG 400, PEG 600, PEG 1500, glycerin, diethylene glycol monoethyl ether (Transcutol®, diethylene glycol ethyl ether or 2-(2-ethoxyethoxy)ethanol), triacetin (glycerin triacetate), and propylene glycol (PG), which solvents may be used alone or as a combination of two or more solvents, with water-miscible solvents comprising, on weight-to-weight (w/w) basis relative to total weight of a formulation of 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20%. In general, the compositions of the invention contain no more than 20% of PG, no more than 20% of glycerin, and no more than 20% of both PG and glycerin when both are present. Preferably, the compositions of the invention contain 6-20%, 8-18%, 6-16%, 6-14%, 8-16%, 8-14%, or 8-12% of PG. Likewise, the compositions of the invention contain 6-20%, 8-18%, 6-16%, 6-14%, 8-16%, 8-14%, or 8-12% of glycerin.

As user herein, the term "antimicrobial agent", or "antimicrobial agents", or "antimicrobial", or "antimicrobials", or "preservative", or "preservatives" refers to substances that inhibit growth or kill microorganisms, whether antibacterial and/or antifungal agents and whether water-soluble and/or insoluble, such as, for example, methyl paraben (methylparaben), ethyl paraben (ethylparaben), propyl paraben (propylparaben), butyl paraben (butylparaben), and heptyl paraben (heptylparaben), benzoic acid and benzoic acid salts such as sodium benzoate, dehydroacetic acid and sodium dehydroacetate, sorbic acid and its salts such as sodium sorbate, salicylic acid and its salts such as sodium salicylate, p-anisic acid, caprylhydroxamic acid, caprylic acid and its salts such as sodium caprate, levulinic acid and its salts such as sodium levulinate, undecylenic (10-undecenoic) acid and its salts such as sodium undecylenate, eugenol, menthol, 1,2-pentanediol, 1,2-hexanediol, 1,2-octanediol, 1,2-decanediol, ethylhexylglycerin, glyceryl caprate, glyceryl caprylate, glyceryl undecylenate, phenethyl alcohol, and phenylpropanol, or may be contained in plant extracts such as, for example, rosmarinic acid and carnosic acid found in rosemary extracts. The antimicrobial agents, whether used singly or as a blend of two or more antimicrobial agents, are to be used in the concentrations that vary from agent to agent and are to be introduced into the formulations in either organic or aqueous phase, all of which is known to those skilled in the art.

As used herein, the term "thickener" or "thickening agent" refers to substances, whether gelling or non-gelling, which raise viscosity and which may or may not require pH adjustment or addition of salts (ions) to produce increase in viscosity. Examples of "thickeners" or "thickening agents" are crosslinked polyacrylic acid polymers such as Carbopol® 71G, 940, 971P, 974P, 980, 981, 5984 EP, ETD 2020, Ultrez 10, Pemulen™ TR-1 and TR-2 NF polymers; hydroxyethyl acrylate/sodium acryloyldimethyl taurate copolymers; polyacrylate crosspolymer-6; sodium acrylate/acryloyldimethyltaurate/dimethylacrylamide crosspolymer; hyaluronic acid of average molecular weights of approximately 8,000-13,000, 50,000-75,000, 450,000-500,000, or one million or more Da; hydroxypropyl methylcellulose (HPMC, hypromellose, substitution types 2910, 2208, or 2906) in grades of viscosity of 2% aqueous solution of approximately 3 cP, 4 cP, 5 cP, 15 cP, 50 cP (40-60 cP), 100 cP (80-120 cP), 200-300 cP, 500-1000 cP, 1000-2000 cP, 4000 cP, methylcellulose, hydroxyethyl cellulose in grades of viscosity of 5% aqueous solution of 100 cP, 50-150 cP, of 2% aqueous solution at 20° C. of 200-300 cP, 800-1500 cP, approximately 2000 cP, approximately 3400 cP, or 5000 cP, ethylcellulose, hydroxypropyl cellulose, also gums such as xanthan gum, locust bean gum, guar gum, alginin, as well as agar gum, pectin, K-carrageenan, l-carrageenan, as well as starches such as potato starch, corn (maize) starch, wheat starch, or pea starch. Some of the thickeners are multifunctional substances and in certain compositions a thickener may act as an anti-caking agent and/or a lubricating agent, and/or a humectant. As used herein, the term "lubricating agent" may refer to a thickener or it may refer to a substance that is not a thickener, for example, to lauric acid and its salts such as sodium laurate, or isopropyl myristate.

As used herein, the term cannabidiol (CBD) refers to CBD produced from industrial hemp or from different strains and chemovars of Cannabis sativa and Cannabis indica, or to CBD produced by using yeast or other means utilizing biotechnology, by chemical synthesis, by combination of these methods, or by any other means. CBD may be isolated from plants as a mixture with other plant-derived materials, such as terpenes, flavonoids, etc. or CBD may be a purified substance, and may be amorphous or exist in one or more different crystalline states (polymorphs). In preferred embodiments, CBD is derived from hemp and contains less than 0.3% THC or CBD is derived from hemp and contains less than 0.2% THC. The composition can be applied 1-60 min prior to sexual activity, or 10-60 min, or 5-30 minutes prior to sexual activity, or 10-30 min, preferably, 5-40 min, more preferably 15-20 min, or 15-40 min. In some embodiments, the off-set time following the application of the CBD-containing composition is 0.5-5 hrs, preferably, 1-3 hrs, more preferably 1-2 hrs.

In general, the total amount of CBD per application is from 5 mg to 1,000 mg of CBD, and may be approximately 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 30 mg, 35 mg, 40 mg, 45 mg, 50 mg of CBD, preferably 10-100 mg of CBD, more preferably, 20-40 mg of CBD, most preferably 20 mg. The CBD-containing composition may be applied multiple-times and the total dose may be subject-specific.

In some embodiments, the concentration of CBD in the composition is from 1 mg/ml to 40 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, or 40 mg/ml, preferably, 5 mg/ml to 20 mg/ml, preferably, 7.5 mg/ml to 12.5 mg/ml, more preferably, 10 mg/ml. Alternatively, the concentration of CBD in a formulation may be 1 mg/g, 2 mg/g, 3 mg/g, 4 mg/g, 5 mg/g, 6 mg/g, 7 mg/g, 8 mg/g, 9 mg/g, 10 mg/g, 11 mg/g, 12 mg/g, 13 mg/g, 14 mg/g, 15 mg/g, 16 mg/g, 17 mg/g, 18 mg/g, 19 mg/g, 20 mg/g, 21 mg/g, 22 mg/g, 23 mg/g, 24 mg/g, 25 mg/g, 26 mg/g, 27 mg/g, 28 mg/g, 29 mg/g, 30 mg/g, 31 mg/g, 32 mg/g, 33 mg/g, 34 mg/g, 35 mg/g, 36 mg/g, 37 mg/g, 38 mg/g, 39 mg/g, or 40 mg/g, preferably, 5 mg/g to 20 mg/g, preferably, 7.5 mg/g to 12.5 mg/g, more preferably, 10 mg/g. Alternatively, CBD may be present in a weight to weight (w/w) ratio relative to phospholipid of 1/20, 1/19, 1/18, 1/17, 1/16, 1/15, 1/14, 1/13, 1/12, 1/11, 1/10, 1/9, 1/8, 1/7, 1/6, or 1/5.

As used herein, the term "application" or "applying", or "administration", or "administering" means placing or spreading or rubbing on a quantity of a composition to female subject's genital area(s), such as on or around external genitalia, for example, onto absorptive mucosa, comprising one or more of: the introitus, the vulva, the labia minora, the clitoris and the vaginal vault.

The term "sexual activity" refers to sexual intercourse or other stimulation with a partner or masturbation with or without a partner, and with or without the aid of a vibrator.

Formulation of the invention can be produced by a number of methods, including those described in the Examples and claims below.

This disclosure incorporates by reference prior-filed U.S. provisional patent applications Nos. 62/932,754; 62/932,762; and 62/972,288, which describe methods of making and alternative uses of the compositions of the invention. In the event of any inconsistency between the prior applications and the present disclosure, the latter supersedes the prior applications.

The following examples are not intended to be limiting. Those of skill in the art will, in light of the present disclosure, appreciate that many changes can be made in the specific materials and which are disclosed and still obtain a like or similar result without departing from the spirit and scope of the invention.

EXAMPLES

Example 1. Preparation of Lotion of CBD-Loaded Liposomes

Hydrogenated soya phosphatidylcholine (10.8 grams) and CBD (1.2 grams) were dissolved in propylene glycol (12 mL) by heating in a water bath at 80-90° C. with magnetic stirring. This solution was added, with overhead stirring, over approximately 30 seconds to a solution of ascorbic acid (50 mg) and sodium ascorbate (500 mg) in 100 mL of deionized water pre-warmed in a water bath at 65° C. to form a white suspension. The suspension was stirred at 65° C. bath temperature for approximately 30 minutes then removed from heat with continued stirring. To a warm suspension, with continued stirring, was added 300 mg (0.25% w/w) polyacrylate crosspolymer-6 to form a white lotion.

Example 2. Studies in Women At-Home, Utilizing a Comprehensive Sexual Function Questionnaire Six female volunteers, ages 24-33 years with sexual dysfunction secondary to SSRI therapy participated in an at-home sexual response study utilizing the invention. They received four doses of the composition of invention, identical to, or very similar to the lotion described in Example 1. Each dose was applied by hand to the labia minora (inner lips), vulva (outside of vagina and inside of labia minora) and clitoris, 20 minutes prior to partner or self-stimulation. Each participant made 4 attempts using the invention at intervals no more than once per day and all 4 attempts were completed within 4 weeks. Following the completion of the 4 episodes, the volunteers completed an online questionnaire, which was structured to include the elements of the Female Sexual Function Index (Rosen) and examined desire/interest, arousal, orgasm, overall sexual satisfaction and any personal perspectives on the invention and its effect on their sexual function. Reports of adverse events were also captured. The questionnaire is exemplified in Appendix A.

Appendix A: Manna™ Female Sexual Response Questionnaire © 2019

1. Over the past 4 weeks, when you used the study product, how would you rate your level (degree) of sexual desire or interest?
   A. Higher than usual
   B. As usual
   C. Less than usual 2. Over the past 4 weeks, when you used the study product, how often did you become lubricated ("wet") during sexual activity?
   A. More often than usual
   B. As usual
   C. Less often than usual 3. Over the past 4 weeks, when you used the study product, how often did you maintain your lubrication ("wetness") until completion of sexual activity?
   A. More often than usual
   B. As usual
   C. Less often than usual 4. Over the past 4 weeks, when you used the study product and had sexual stimulation, how often did you reach orgasm (climax)?
   A. More often than usual/Most or all the time
   B. As usual
   C. Less often than usual 5. Over the past 4 weeks, when you used the study product and had sexual stimulation, was the ease of achieving your orgasms:
   A. Easier
   B. As usual
   C. More difficult 6. Over the past 4 weeks, when you used the study product and had sexual stimulation, was the intensity of your orgasms:
   A. More intense
   B. As usual
   C. Less intense 7. Over the past 4 weeks, when you used the study product, how satisfied were you with your ability to reach orgasm (climax) during sexual activity or intercourse?
   A. More satisfied than usual
   B. As satisfied as usual
   C. Less satisfied than usual 8. Over the past 4 weeks, how satisfied have you been with your overall sexual life?
   A. More satisfied than usual
   B. As satisfied as usual
   C. Less satisfied than usual 9. What percentage of your prior sexual function was re-established with Vella™?
   A. 100%
   B. 75%
   C. 50%
   D. 25%
   E. None Example 3. Studies in Women at-Home, Utilizing a Comprehensive Sexual Function Questionnaire—Aggregate Responses of the Study Described in Example 2

The responses in the questionnaires completed by all 6 participants referred to in Example 2 were combined and grouped into domains of Desire (Question 1), Arousal (Questions 2 and 3), and Orgasm (Questions 4, 5, 6, and 7). The aggregated results per category were: Increased Desire was reported by 1 out of 6 participants or 17%; Increased Arousal—frequency and/or ease of lubrication, was reported by 5 out of 6 participants or 83%; Orgasm—frequency, ease, intensity and/or satisfaction, was reported by 6 out of 6 participants or 100%. However, one was only positive in the intensity of orgasm score and was classified as a non-responder. Overall (responders and non-responder), 83% reported increased frequency of orgasm, 67% reported increased ease of orgasm, 50% reported increased intensity of orgasm, and 83% reported increased satisfaction. Additionally, 5/6 reported some return of pre-SSRI sexual function, with the 5 responders indicating that there was 25% to 75% recovery of pre-SSRI sexual function with a median of 75%.

Example 4. At-Home, Self-Reported Effects on Sexual Function of a 27-Year-Old Woman Taking Sertraline for Depression The participant was one of the 6 volunteers referred to in Example 2 and the study was conducted as described therein. She complained of sexual dysfunction, specifically anorgasmia within 2 weeks of institution of sertraline (Zoloft®) therapy.

She reported the following positive outcomes:
1. Over the 4 weeks, when she used the invention, she became lubricated ("wet") more often during sexual activity;
2. Over the past 4 weeks, when she used the invention, she maintained lubrication ("wetness") more often during sexual activity;
3. Over the past 4 weeks, when she used the invention and had sexual stimulation, she reached orgasm (climax) more often/most of the time than usual;
4. Over the past 4 weeks, when she used the invention and had sexual stimulation, she experienced greater ease of achieving orgasms than usual;
5. Over the past 4 weeks, when she used the invention, she was more satisfied with her ability to reach orgasm (climax) during sexual activity or intercourse than usual;
6. Over the past 4 weeks, she reported that with utilization of the product, she had return of 75% of pretreatment sexual function;
7. No adverse events were reported.

The following was her self-reported testimonial:
"I recently went on a [SSRI] medication while dealing with some trauma. I was told by both my doctor and several friends that it might affect my libido, as well as my ability to orgasm. Within two weeks of taking the prescribed SSRI I suddenly lost my ability to orgasm, which had previously never been a problem. Without fail, every single time I use Vella, I am able to reach orgasm with pleasure and ease. Vella has allowed me to take care of my mental health and remain on the medication needed, without also sacrificing my sexual wellness and pleasure. I would recommend Vella to anyone dealing with a similar issue as the number one product to use. Not only does Vella improve ease of orgasm, but it also makes them feel longer and a bit more intense".

Example 5. At-Home, Self-Reported Effects on Sexual Function of a 28-Year-Old Woman Taking Sertraline for Depression The participant was one of the 6 volunteers referred to in Example 2 and the study was conducted as described therein. She complained of sexual dysfunction, specifically decreased desire and difficulties with orgasm, after the institution of sertraline (Zoloft) therapy.

She reported the following positive outcomes:
1. Over the past 4 weeks, when she used the study product, she reported a higher level (degree) of sexual desire or interest, than usual
2. Over the 4 weeks, when she used the invention, she became lubricated ("wet") more often during sexual activity;
3. Over the past 4 weeks, when she used the invention, she maintained lubrication ("wetness") more often during sexual activity;
4. Over the past 4 weeks, when she used the invention and had sexual stimulation, she reached orgasm (climax) more often/most of the time than usual.
5. Over the past 4 weeks, when she used the invention and had sexual stimulation, she experienced greater ease of achieving orgasms than usual;
6. Over the past 4 weeks, when she used the study product and had sexual stimulation, she experienced more intense orgasms;
7. Over the past 4 weeks, when she used the invention, she was more satisfied with her ability to reach orgasm (climax) during sexual activity or intercourse than usual;
8. Over the past 4 weeks, she reported that with utilization of the product, she had return of 75% of pretreatment sexual function;
9. No adverse events were reported.

The following was her self-reported testimonial:
"Vella restored the sex drive that I lost when I started taking antidepressants. Before, I felt that with anti-depressants I had to choose between my mental health and my sexual wellness, and Vella gives me the opportunity to have both at the same time. I no longer need to sacrifice my sexual life for my mental health and vice versa. Vella not only increased my sexual drive, but it made my orgasms much easier to achieve, and definitely increased the intensity of them. My orgasms while using Vella are actually even better than the ones I had before starting anti-depressants. Vella increased my sex drive much more than I expected and it's such a relief to know I can still have a normal sex life while taking care of my mental health".

Example 6. At-Home, Self-Reported Effects on Sexual Function of a 25-Year-Old Woman Taking Sertraline for Depression The participant was one of the 6 volunteers referred to in Example 2 and the study was conducted as described therein. She complained of sexual dysfunction after the institution of sertraline (Zoloft®) therapy early in her life.

She reported the following positive outcomes:
1. Over the 4 weeks, when she used the invention, she became lubricated ("wet") more often during sexual activity;
2. Over the past 4 weeks, when she used the invention, she maintained lubrication ("wetness") more often during sexual activity;
3. Over the past 4 weeks, when she used the invention and had sexual stimulation, she reached orgasm (climax) more often/most of the time than usual.
4. Over the past 4 weeks, when she used the invention and had sexual stimulation, she experienced greater ease of achieving orgasms than usual;
5. Over the past 4 weeks, when she used the invention, she was more satisfied with her ability to reach orgasm (climax) during sexual activity or intercourse than usual;
6. Over the past 4 weeks, she reported that with utilization of the product, she had return of 50% of pretreatment sexual function;
7. No adverse events were reported.

The following was her self-reported testimonial:

"Vella has given me an alternative to what I thought would be a life-long difficulty of achieving physical arousal due to my SSRI's. Rather than having to alter the dosage of a medication which helps me overcome the daily obstacles of depression and anxiety with ease, I am able to be intimate with myself or a partner without sacrificing my mental wellbeing. I found it much easier to become physically aroused by using Vella™, which helped me achieve orgasm much faster than usual! In the past, it would often take a long time to achieve orgasm (even with the CBD lubricants on the market today, many claiming the user will experience ease of orgasm by using it.) However, Vella's absorption into the soft tissue promotes physical arousal, which is unlike anything I had ever used before. I would definitely recommend Vella to a friend, especially to any friends who are struggling with physical arousal due to SSRI usage. Vella has made a world of difference in my sexual wellness as a someone who has been on SSRI's for several years now. Any friends of mine who have begun SSRI's and feel frustrated with the side effects".

Example 7. At-Home, Self-Reported Effects on Sexual Function of a 32-Year-Old Woman Taking Sertraline for Depression The participant was one of the 6 volunteers referred to in Example 2 and the study was conducted as described therein. She complained of sexual dysfunction, specifically after the institution of sertraline (Zoloft) therapy.

She reported the following positive outcomes:
1. Over the past 4 weeks, when she used the invention and had sexual stimulation, she reached orgasm (climax) more often/most of the time than usual.
2. Over the past 4 weeks, when she used the invention and had sexual stimulation, she experienced greater ease of achieving orgasms than usual;
3. Over the past 4 weeks, when she used the invention, she was more satisfied with her ability to reach orgasm (climax) during sexual activity or intercourse than usual;
4. Over the past 4 weeks, she reported that with utilization of the product, she had return of 50% of pretreatment sexual function;
5. No adverse events were reported.

Example 8. At-Home, Self-Reported Effects on Sexual Function of a 33-Year-Old Woman Taking Citalopram for Depression The participant was one of the 6 volunteers referred to in Example 2 and the study was conducted as described therein. She complained of sexual dysfunction secondary to citalopram (Celexa®) therapy. She was not sexually active before starting therapy.

She reported the following positive outcomes:
1. Over the 4 weeks, when she used the invention, she became lubricated ("wet") more often during sexual activity;
2. Over the past 4 weeks, when she used the study product and had sexual stimulation, she experienced more intense orgasms;
3. No adverse events were reported.

Example 9. At-Home, Self-Reported Effects of a CBD Tincture on Sexual Function of 27-Year-Old Woman on Sertraline with Anorgasmia The 27-year-old woman in Example 4 underwent a two week wash out period with no cannabinoid or *Cannabis* exposure. She then repeated the 4-week study with oral tincture of CBD at approximately 20 mg per dosage prior to sexual activity. The subsequent results from the end of study questionnaire indicated there was no change in the domains of desire or arousal, and there was continued anorgasmia.

Example 10. Preparation of Lotion of THC-Loaded Liposomes

Hydrogenated soya phosphatidylcholine (5.61 grams) and THC extract of known purity equivalent to 623.8 mg of THC, are dissolved in propylene glycol (7.4 mL) by heating in a water bath at 80-90° C. with magnetic stirring. This solution is added, with overhead stirring to a solution of ascorbic acid (26 mg) and sodium ascorbate (260 mg) in 51.7 mL of deionized water pre-warmed in a water bath at 65° C. to form a white suspension. The suspension is stirred at 65° C. bath temperature for approximately 30 minutes and 62.3 mg (0.1% w/w) polyacrylate crosspolymer-6 is added. The resultant mixture is then removed from heat and allowed to cool to ambient temperature with continued stirring.

Example 11. At-Home, Self-Reported Effects of a THC Liposomal Lotion on Sexual Function of a Pre-Menopausal Women Taking Antidepressants Subjects described in Example 2, undergo a two-week washout period followed by an identical 4-week trial of liposomal THC utilizing the same methodology as for the CBD version, prepared as described in Example 10. At the end of the 4 weeks, both subjects report no change in desire, arousal or orgasm. Additionally, neither subject reports any psychoactivity or THC intoxication ("high").

The invention claimed is:

1. A method of treating female sexual dysfunction induced by one or more antidepressants, previously administered to a female subject, the method comprising applying topically a composition consisting of CBD as the sole active ingredient ("CBD-containing composition"), said composition being applied to the mucosal surface of female subject's genital arousal area(s), wherein the composition is applied in an amount and for a period of time prior to a sexual activity such that sexual dysfunction of the subject is ameliorated during the sexual activity.

2. The method of claim 1, wherein said topical composition is formulated as a lotion, an ointment, a cream, a suspension, a paste, a gel, a balm, a tincture, an emulsion, or a serum, any one of which is applied to the female genitalia.

3. The method of claim 1, wherein the genital area includes genitalia with absorptive mucosa, comprising one or more of: the introitus, the vulva, the labia minora, the clitoris and the vaginal vault.

4. The method of claim 1, wherein the antidepressant causing sexual dysfunction is selected from an SSRI, an SNRI, a tricyclic antidepressant, and a tetracyclic antidepressant.

5. The method of claim 4, wherein a) the SSRI is selected from sertraline, citalopram, fluoxetine, escitalopram, paroxetine, fluvoxamine, duloxetine, venlafaxine, and desvenlafaxine; b) the SNRI is selected from duloxetine, venlafaxine, desvenlafaxine, milnacipran, and levomilnacipran; c) the tricyclic antidepressant is selected from clomipramine, trimipramine, amitriptyline, desipramine, imipramine, lofepramine, doxepin, nortriptyline, amoxapine, and protriptyline; and/or the tetracyclic antidepressant is selected from maprotiline and mirtazapine.

6. The method as in claim 1, wherein the female subject is human and has been diagnosed with one or more disorders or conditions, treated by taking an anti-depressant, selected from the group consisting of major depressive disorder (MDD), persistent depressive disorder or dysthymia, and melancholic depression.

7. The method of claim 1, wherein the female sexual dysfunction is characterized by one or more of the following characteristics: difficulty achieving arousal and/or insufficient lubrication, difficulty in achieving and maintaining engorgement, and difficulty in achieving and maintaining lubrication.

8. The method of claim 1, wherein the female sexual dysfunction is characterized by one or more of the following characteristics: difficulty achieving orgasm, low orgasm intensity, or anorgasmia.

9. The method of claim 1, wherein the female sexual dysfunction is characterized to lack of sexual desire or interest.

10. The method of claim 1, wherein the female subject is premenopausal.

11. The method of claim 1, wherein the female subject is post-menopausal.

12. The method as in claim 1, wherein the subject has been previously treated with, but did not satisfactorily respond to, one or more of the following treatments: (1) change of the time the antidepressant medication is taken, (2) drug holidays, (3) decrease the dose of the medication, (4) switching to or addition of mirtazapine, (5) switching to or addition of bupropion, (6) topical testosterone, (7) amantadine, (8) switching to or addition of trazodone, (9) methylphenidate, (10) behavioral therapy, and (11) acupuncture.

13. The method as in claim 1, wherein the female subject is further treated with one or more of the following treatments: (1) change of the time the antidepressant medication is taken, (2) drug holidays, (3) decrease the dose of the medication, (4) switching to or addition of mirtazapine, (5) switching to or addition of bupropion, (6) topical testosterone, (7) acupuncture, (8) amantadine, (9) switching to or addition of trazodone, (10) methylphenidate, (11) behavioral therapy, and (12) dietary supplements.

14. The method of claim 1, wherein the amelioration of the sexual dysfunction is exhibited by one or both of the following parameters:
   i) clitoral smooth muscle relaxation;
   ii) increased vaginal and clitoral blood flow.

15. The method of claim 1, wherein the amelioration of the sexual dysfunction is exhibited by one or more of the following subjectively self-reported outcomes including:
   i) "increased lubrication/wetness during sexual activity";
   ii) "reaching orgasm more often";
   iii) "greater ease or achieving orgasm";
   iv) "being more satisfied";
   v) "higher level of sexual desire"; and
   vi) "reduction in pain during sexual activity".

16. The method of claim 1, wherein the total amount of CBD applied is from 5 mg to 1,000 mg of CBD.

17. The method of claim 16, wherein the total amount of CBD applied is 10-100 mg of CBD.

18. The method of claim 17, wherein the total amount of CBD application is 20-40 mg of CBD.

19. The method of claim 1, wherein the composition is applied 1-60 min prior to sexual activity.

20. The method of claim 1, wherein the CBD-containing composition is applied at 5-30 mins prior to the sexual activity.

21. The method of claim 1, wherein CBD is hemp-derived and/or contains less than 0.3% THC by weight.

22. The method of claim 1, wherein the CBD-containing composition is provided in a single-use container.

23. The method of claim 1, wherein the CBD-containing composition further comprises preservative(s) and is provided in a multi-use container.

24. The method of claim 1, wherein the concentration of CBD in the composition is from 1 mg/mL to 40 mg/mL.

25. The method of claim 1, wherein the subject is afflicted with a disorder selected from (1) Sexual Interest/Arousal Disorder (SIAD) and (2) Female Orgasmic Disorder.

26. The method of claim 25, wherein the subject, upon having been treated with the CBD-containing composition for 3-6 months, reports arousal and or orgasmic improvements as measured by FSFI, wherein the improvement in sexual interest/arousal domain is by 1-2 points, and by 1-2 points in the orgasm domain of the FSFI.

27. The method of claim 1, wherein off-set time following the application of the CBD-containing composition is 0.5-5 hrs.

28. The method as in claim 1, wherein the subject was previously treated with an anti-depressant that induced sexual dysfunction and has persistent sexual dysfunction despite discontinuation of the anti-depressant therapy.

* * * * *

UNITED STATES PATENT AND TRADEMARK OFFICE
CERTIFICATE OF CORRECTION

| | | |
|---|---|---|
| PATENT NO. | : 11,717,495 B2 | Page 1 of 1 |
| APPLICATION NO. | : 17/165002 | |
| DATED | : August 8, 2023 | |
| INVENTOR(S) | : Harin Padma-Nathan et al. | |

It is certified that error appears in the above-identified patent and that said Letters Patent is hereby corrected as shown below:

On the Title Page

In Item (71) delete the address "Worcester, MA" and add --Tulsa, OK--.

In Item (72) delete the name "MIchael Frid" and add --Michael Frid--.

In Item (72) after the name Nial Chase Demena delete "Worceseter" and add --Worcester--.

In Item (73) delete the address "Worcester, MA" and add --Tulsa, OK--.

Signed and Sealed this
Seventh Day of January, 2025

Derrick Brent
*Acting Director of the United States Patent and Trademark Office*